United States Patent [19]
Tanouchi et al.

[11] 4,446,143
[45] May 1, 1984

[54] RHODANINE DERIVATIVES

[75] Inventors: Tadao Tanouchi, Takatsuki; Satoshi Shigeoka, Neyagawa; Masanori Kawamura, Ibaraki; Masaki Hayashi; Hiroshi Terashima, both of Takatsuki; Fumio Hirata, Suita, all of Japan

[73] Assignee: Ono Pharmaceutical Co., Ltd., Osaka, Japan

[21] Appl. No.: 286,839

[22] Filed: Jul. 27, 1981

[30] Foreign Application Priority Data

Jul. 28, 1980 [JP] Japan .................. 55-102410

[51] Int. Cl.$^3$ ................. C07D 277/36; A61K 31/425
[52] U.S. Cl. .................... 424/270; 546/135; 546/275; 548/181; 548/183; 424/258; 424/263
[58] Field of Search .............. 548/183, 181; 546/135, 546/275; 424/270

[56] References Cited

FOREIGN PATENT DOCUMENTS 55-33103  3/1980  Japan .................. 548/183
56-111849 9/1981  Japan .

OTHER PUBLICATIONS

Minka, Farmartseut. Zh, (Kiev), 18(5), 32–5, (1963), Abstract only.
Bulan et al., Farmartseut. Zh, (Kiev), (1), 49–52, (1978), Abstract only.

*Primary Examiner*—Robert Gerstl
*Attorney, Agent, or Firm*—Sughrue, Mion, Zinn, Macpeak & Seas

[57] ABSTRACT

The rhodanine derivatives of the general formula:

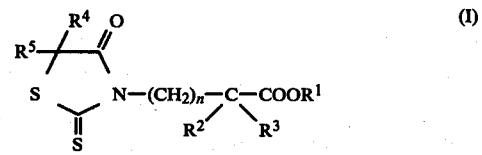

possess a strong inhibitory activity on aldose reductase, and are useful for the prevention and treatment of nerve disturbances such as neuralgia, retinopathy, diabetic cataract and renal disturbances such as tubular nephropathy.

41 Claims, No Drawings

RHODANINE DERIVATIVES

This invention relates to novel rhodanine derivatives, process for their preparation and an aldose reductase inhibitor containing the derivative as a main ingredient.

Hitherto, various compounds have been proposed for treating diabetes resulting from an increased blood sugar level due to deficient insulin secreted from pancreas. However, there are not so many compounds which are sufficiently satisfactory as drugs for the prevention or treatment of complications of chronic diabetes, particularly those ascribed to an aldose reductase such as retinopathy, diabetic cataract, nerve disturbances and renal disorders. An aldose reductase is an enzyme which reduces an aldose in human beings or other animals, for example, glucose or galactose, into the corresponding polyol, for example, sorbitol or galactitol. The sorbitol and galactitol produced by the action of this enzyme are accumulated in the crystalline lenses, the peripheral nerves, the kidney, etc. of diabetics and galactosemiacs thus causing the abovedescribed complications [cf. Jap. J. Opthalmol., 20, 399 (1976), Int. Congr. Ser. Excerpta Med., 403, 594 (1977) and Metabolism, 28, 456 (1979)].

The present inventors have conducted extensive investigations on compounds useful for preventing or treating the above-described complications of chronic diabetes by inhibiting the functions of the aldose reductase, and found that the rhodanine derivatives of the present invention are useful as an aldose reductase inhibitor, and thus completed the present invention.

The present invention relates to rhodanine derivatives represented by the general formula:

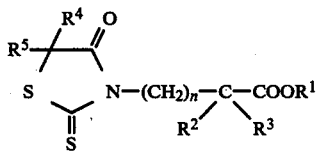

(wherein $R^1$ represents a hydrogen atom, an alkyl group of 1-12 carbon atoms, an aralkyl group of 7-13 carbon atoms, a cycloalkyl group of 4-7 carbon atoms which is unsubstituted or substituted by at least one alkyl group of 1-4 carbon atoms, or a phenyl group which is unsubstituted or substituted by at least one halogen atom, trifluoromethyl group, phenyl group, nitro group, hydroxyl group, carboxyl group, amino group which may be substituted by an alkyl group of 1-4 carbon atoms, or alkyl, alkoxy or alkylthio group of 1-4 carbon atoms; $R^2$ and $R^3$, which may be the same or different with each other, each represents a hydrogen atom, an alkyl group of 1-4 carbon atoms, or a phenyl group which is unsubstituted or substituted by at least one halogen atom, trifluoromethyl group, phenyl group, nitro group, hydroxyl group, carboxyl group, amino group which may be substituted by an alkyl group of 1-4 carbon atoms, or alkyl, alkoxy or alkylthio group of 1-4 carbon atoms; $R^4$ represents an alkyl group of 1-4 carbon atoms, a cycloalkyl group of 4-7 carbon atoms which is unsubstituted or substituted by at least one alkyl group of 1-4 carbon atoms, a phenyl or benzyl group which is unsubstituted or substituted by at least one halogen atom, trifluoromethyl group, phenyl group, nitro group, hydroxyl group, carboxyl group, amino group which may be substituted by an alkyl group of 1-4 carbon atoms, or alkyl, alkoxy or alkylthio group of 1-4 carbon atoms, a naphthyl group, an anthracenyl group, or a heterocyclic group containing at least one of nitrogen, oxygen and sulfur atoms which is unsubstituted or substituted by at least one halogen atom, trifluoromethyl group, phenyl group, nitro group, hydroxyl group, carboxyl group, amino group which may be substituted with an alkyl group of 1-4 carbon atoms, or alkyl, alkoxy or alkylthio group of 1-4 carbon atoms; $R^5$ represents a hydrogen atom, an alkyl group of 1-4 carbon atoms, a cycloalkyl group of 4-7 carbon atoms which is unsubstituted or substituted by at least one alkyl group of 1-4 carbon atoms, a phenyl or benzyl group which is unsubstituted or substituted by at least one halogen atom, trifluoromethyl group, phenyl group, nitro group, hydroxyl group, carboxyl group, amino group which may be substituted by an alkyl group of 1-4 carbon atoms, or alkyl, alkoxy or alkylthio group of 1-4 carbon atoms, a naphthyl group, an anthracenyl group, or a heterocyclic group containing at least one of nitrogen, oxygen and sulfur atoms which is unsubstituted or substituted by at least one halogen atom, trifluoromethyl group, phenyl group, nitro group, hydroxyl group, carboxyl group, amino group which may be substituted by an alkyl group of 1-4 carbon atoms, or alkyl, alkoxy or alkylthio group of 1-4 carbon atoms; and n represents 0, 1 or 2; with the proviso that when $R^5$ represents a hydrogen atom, $R^4$ does not represent an alkyl group of 1-4 carbon atoms) and, when $R^1$ represents a hydrogen atom, a non-toxic salt of the acid.

"Alkyl group" used throughout the specification including claims means a straight chain or branched chain alkyl group.

The alkyl group of 1-12 carbon atoms represented by $R^1$ includes a methyl, ethyl, propyl, butyl, pentyl, hexyl, heptyl, octyl, nonyl, decyl, undecyl and dodecyl group, and isomers thereof. The aralkyl group of 7-13 carbon atoms represented by $R^1$ includes benzyl, 1-phenylethyl, 2-phenylethyl, 3-phenylbutyl, 4-phenylbutyl, 1-(2-naphthyl)ethyl, 2-(1-naphthyl)ethyl and biphenylmethyl groups. The cycloalkyl group of 4-7 carbon atoms which is unsubstituted or substituted by at least one alkyl group of 1-4 carbon atoms as represented by $R^1$, $R^4$ or $R^5$ includes cyclobutyl, 1-propylcyclobutyl, 1-butylcyclobutyl, 2-methylcyclobutyl, 2-propylcyclobutyl, 3-ethylcyclobutyl, 3-propylcyclobutyl, 2,3,4-triethylcyclobutyl, cyclopentyl, 3-ethylcyclopentyl, 3-propylcyclopentyl, 3-butylcyclopentyl, 3-tert-butylcyclopentyl, 2,2-dimethylcyclopentyl, (1-methyl-3-propyl)cyclopentyl, (2-methyl-3-propyl)cyclopentyl, (2-methyl-4-propyl)-cyclopentyl, cyclohexyl, 3-ethylcyclohexyl, 3-isopropylcyclohexyl, 4-methylcyclohexyl, 4-ethylcyclohexyl, 4-propylcylohexyl, 4-tert-butylcyclohexyl, 2,2-dimethylcyclohexyl, 2,6-dimethylcyclohexyl, (2,6-dimethyl-4-propyl)cyclohexyl, and cycloheptyl groups, etc.

The phenyl group and the phenyl moiety of the benzyl group which are unsubstituted or substituted by at least one halogen atom, trifluoromethyl group, phenyl group, nitro group, hydroxyl group, carboxyl group, amino group which may be substituted by an alkyl group of 1-4 carbon atoms, or alkyl, alkoxy or alkylthio group of 1-4 carbon atoms as represented by $R^1$, $R^2$, $R^3$, $R^4$ or $R^5$ includes phenyl, 2-, 3- or 4-bromophenyl, 2-, 3- or 4-chlorophenyl, 2,4-dichlorophenyl, 2,4,6-trichlorophenyl, 2,3,4,5,6-pentafluorophenyl, 2-, 3- or 4-tolyl, 2-, 3- or 4-ethylphenyl, 2-, 3- or 4-isopropylphenyl, 2-, 3- or 4-tert-butylphenyl, 4-sec-butylphenyl, 2,4-dimethylphenyl, 2,5-dimethylphenyl, 2,6-dimethylphenyl, 2,6-diethylphenyl, (2-isopropyl-5-methyl)phenyl, 2,6-diisopropylphenyl, (2-tert-butyl-6-methyl)phenyl, (2-tert-butyl-4-methyl)phenyl, 2,4-di-tert-butylphenyl, 2,6-di-tert-butylphenyl, 3,5-di-tert-butylphenyl, 2,4,6-trimethylphenyl, (2-tert-butyl-4,6-dimethyl)phenyl, (2,6-di-tert-butyl-4-methyl)phenyl, 2,4,6-tri-tert-butylphenyl, 3-trifluoromethylphenyl, 4-biphenyl, 2-, 3- or 4-methoxyphenyl, 2-, 3- or 4-ethoxyphenyl, 2-, 3- or 4-methylthiophenyl, 2-, 3- or 4-ethylthiophenyl, 2-, 3- or 4-hydroxyphenyl, 2-, 3- or 4-nitrophenyl, 2-, 3- or 4-carboxyphenyl, 2-hydroxy-5-chlorophenyl, 2-, 3- or 4-aminophenyl, 4-(N,N-dimethyl)aminophenyl, 4-(N,N-diethyl)aminophenyl and 3,4-dimethoxyphenyl groups, etc.

The heterocyclic group containing at least one of nitrogen, oxygen and sulfur atoms which is unsubstituted or substituted by at least one halogen atom, trifluoromethyl group, phenyl group, nitro group, hydroxyl group, carboxyl group, amino group which may be substituted by an alkyl group of 1-4 carbon atoms, or alkyl, alkoxy or alkylthio group of 1-4 carbon atoms as represented by $R^4$ or $R^5$ includes 3-pyridyl, 4-pyridyl, 2-thienyl, 2-furyl, 3-pyrrolyl, 3-indolyl, 5-indolyl, 5-bromo-3-indolyl, 5-chloro-3-indolyl, 5-methoxy-3-indolyl, 5-nitro-3-indolyl, 5-carboxy-3-indolyl, 1-methyl-3-indolyl, 2-methyl-3-indolyl, 2-isopropyl-3-indolyl, 2-phenyl-3-indolyl, 5-nitro-2-furyl, 3-quinolyl, 3-benzo[b]furyl, 3-benzo[b]thienyl and 4-oxo-2-chromanyl groups, etc.

The alkyl group of 1-4 carbon atoms represented by $R^2$, $R^3$, $R^4$ or $R^5$ includes methyl, ethyl, propyl, isopropyl, butyl, isobutyl, sec-butyl and tert-butyl groups.

Preferable $R^1$ are a hydrogen atom and an alkyl group of 1-12 carbon atoms, more preferably a hydrogen atom and an alkyl group of 1-4 carbon atoms, and most preferably a hydrogen atom.

$R^2$ and $R^3$ are preferably both hydrogen atoms or methyl groups, or one of them is preferably a hydrogen atom with another being a methyl group or a phenyl group. More preferably, both are hydrogen atoms.

According to the present invention, the rhodanine derivatives represented by the general formula (I) may be obtained by reacting a compound represented by the general formula:

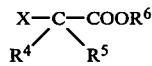

(wherein X represents a halogen atom; $R^6$ represents a hydrogen atom, an alkali metal or an alkyl group of 1-4 carbon atoms; and $R^4$ and $R^5$ represent the same meanings as described above) with a compound represented by the general formula:

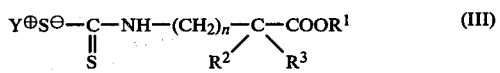

[when $R^1$ = H, $-COO^{\ominus}Y^{\oplus}$]

(wherein Y represents an alkali metal, alkaline earth metal or ammonium ion; and the other symbols represent the same meanings as described above) in an aqueous solution or a water-containing alkanol of 1-4 carbon atoms, for example water-containing methanol or water-containing ethanol, in the presence or absence of potassium iodide at a temperature ranging from a refluxing temperature of a reaction solvent to 0° C., and subsequently subjecting the reaction product to a reaction using an acid, for example an inorganic acid such as hydrochloric acid or an organic acid such as p-toluenesulfonic acid, or to a heating reaction by refluxing in an inert organic solvent, such as benzene, toluene or xylene.

The resulting product may be purified by known purification means, for example, recrystallization or thin layer, column or high speed liquid chromatography using silica gel, and the like.

The compound represented by the general formula (II) is well known per se or may easily be prepared by a known process, for example, by halogenating an α-substituted acetic acid represented by the general formula:

(wherein all the symbols represent the same meanings as described above) using a known technique for halogenation, such as a reaction using phosphorus tribromide and bromine, or a method disclosed in J. Org. Chem., 40, 3420 (1975), or through the reaction steps described in the following scheme A. In the formulae, all the symbols represent the same meanings as described above.

Scheme A

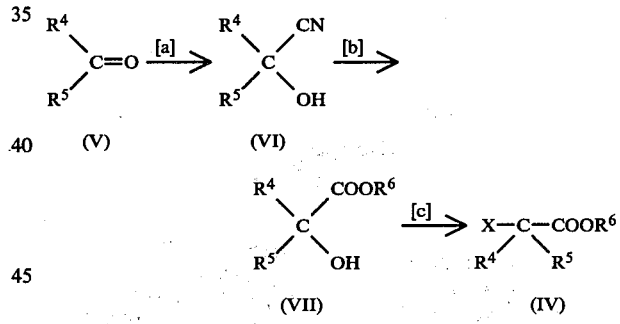

Each of the steps [a], [b] and [c] in the scheme A may easily be carried out using known methods. For example, the step [a] may be performed in an aqueous solution at room temperature using sodium hydrogen-sulfite and sodium cyanide; the step [b] may be performed by hydrolyzing at room temperature using hydrochloric acid, if desired, followed by esterification using the corresponding alcohol in the presence of an acid catalyst; and the step [c] may be conducted using phosphorus tribromide at room temperature.

The compound represented by the general formula (III) may be obtained by reacting a compound represented by the general formula:

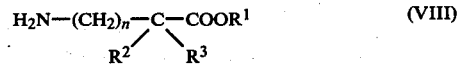

(wherein all the symbols represent the same meanings as described above) with carbon disulfide in the presence of aqueous ammonia or an aqueous solution of an alkali metal or alkaline earth metal hydroxide, e.g., potassium hydroxide or sodium hydroxide, at a temperature ranging from room temperature to 0° C. [cf. Yakugaku Zasshi, 79, 1465 (1959) or Chem. Ber., 41, 1901 (1908)].

The starting materials represented by the general formulae (IV), (V) and (VIII) are known per se or may be prepared by known processes.

The esters represented by the general formula (I) wherein $R^1$ represents the group other than a hydrogen atom with the other symbols representing the same meanings as described above may be obtained by esterifying the corresponding carboxylic acids represented by the general formula (I) wherein $R^1$ represents a hydrogen atom and the other symbols representing the same meanings as described above, by methods known per se. Processes for esterification of carboxylic acids are well known. For example, the esterification can be conducted by (1) a process of using a diazoalkane, or (2) a process of using an N,N-dimethylformamide-dialkylacetal [cf. Helv. Chim. Acta., 48, 1746 (1965)] in case where $R^1$ represents an alkyl group, or (3) a process of using an alkyl halide or an aralkyl halide in case where $R^1$ represents an alkyl group or an aralkyl group, or (4) a process of using dicyclohexylcarbodiimide [cf. the specification of Japanese Patent No. 762305], (5) a process of using a pivaloyl halide [cf. the specification of Japanese Patent No. 756972], (6) a process of using an alkylsulphonyl halide or an arylsulphonyl halide [cf. the specification of Japanese Patent No. 759351], (7) a process of using isobutyl chloroformate [cf. the specification of British Pat. No. 1,492,439], (8) a process of using dipyridyl disulphide and triphenylphosphine [cf. Tetrahedron Letters, 3409 (1976)], or a process as disclosed in "Compendium of Organic Synthetic Methods", Section 107 of Vol. 1 (1971), Vol. 2 (1974) and Vol. 3 (1977) published by John Wiley & Sons, Inc. (U.S.A.) in case wherein $R^1$ represents an alkyl group or an aralkyl group or another esterifiable functional group within the definition of $R^1$.

The compounds represented by the general formula (I) wherein $R^1$ represents a hydrogen atom may be converted into their salts by known methods. Preferably, the salts are non-toxic salts. The term "non-toxic salts" used in this specification mean salts of cations of which are relatively innocuous to the animal organism, when used in an amount required for the treatment, so that the beneficial pharmacological properties of the compounds represented by the general formula (I) are not vitiated by the side-effects ascribable to those cations. The salts are preferably water-soluble. Suitable salts include salts of alkali metals such as sodium or potassium, salts of alkaline earth metals such as calcium or magnesium, ammonium salts and pharmaceutically acceptable (i.e., non-toxic) amine salts. Suitable amines which form such salts with carboxylic acids are well known and include, for example, amines derived in theory by the replacement of one or more of the hydrogen atoms of ammonia by other groups. Such groups, which may be the same or different with each other when more than one hydrogen atom is replaced, are selected from, for example, alkyl groups of 1–6 carbon atoms and hydroxyalkyl groups of 2 or 3 carbon atoms. As a preferred non-toxic amine salt, there are illustrated a tetraalkylammonium salts such as tetramethylammonium salts and organic amine salts such as methylamine salts, ethylamine salts, isopropylamine slats, tert-butylamine salts, dimethylamine salts, cyclopentylamine salts, benzylamine salts, phenethylamine salts, piperidine salts, monoethanolamine salts, diethanolamine salts, lysine salts and arginine salts.

The salts may be prepared from the acids represented by the general formula (I) wherein $R^1$ represents a hydrogen atom according to known methods, for example, by reaction of stoichiometric quantities of an acid represented by the general formula (I) and an appropriate base, such as a hydroxide or carbonate of an alkali metal or alkaline earth metal, ammonium hydroxide, ammonia or an organic amine in a suitable solvent. The salts may be isolated by lyophilisation of the solution, or, if it is sufficiently insoluble in the reaction solvent, by filtration, if necessary after removal of part of the solvent.

Since the novel rhodanine derivatives of the present invention possess an activity of inhibiting an aldose reductase which reduces an aldose to the corresponding polyol, they are useful as an aldose reductase inhibitor. This means that they are useful for the prevention and treatment of nerve disturbances such as neuralgia, retinopathy, diabetic cataract and renal disturbances such as tubular nephropathy which are known as complications due to an aldose reductase among the complications of chronic diabetes such as circulatory disturbances, renal disturbances, retinopathy, diabetic cataract, nerve disturbances, infections, etc. [cf. Jap. J. Ophthalmol., 20, 399 (1976), Int. Congr. Ser. Excerpta Med., 403, 594 (1977) and Metabolism, 28, 456 (1979)].

For example, according to experiments in a laboratory conducted in accordance with the method as described in J. Biol. Chem., 240, 877 (1965) using an aldose reductase obtained from the crystalline lenses of rats, the rhodanine derivatives represented by the general formula (I) produced a 50% inhibition of the aldose reductase at $10^{-5}$–$10^{-9}$ M concentrations. Further, the effect of inhibiting accumulation of sorbitol in the sciatic nerve of a streptozotocin-induced diabetic rat was examined according to the method as described in the specification of U.S. Pat. No. 3,821,383 and, as a result, the rhodanine derivatives of the present invention significantly inhibited the accumulation without showing any toxicity.

Furthermore, experiments on cytotoxicity were conducted using Raji cells, and the 50% growth inhibition concentrations ($TCID_{50}$) of the compounds of the present invention were 20 μg/ml or more.

The present invention additionally includes in its scope pharmaceutical compositions containing at least one of the rhodanine derivatives of the present invention or non-toxic salts thereof as a main ingredient, together with a pharmaceutically inert carriers or coating. These pharmaceutical compositions may be prepared by conventional processes well-known to the art. Examples of such compositions include tablets, pills, powders, granules, capsules, suppositories, injections, eye drops and the like. These pharmaceutical compositions are clinically administered orally, intrarectally, parenterally (e.g., intravenously, intramuscularly, subcutaneously or intraperitoneally), or as eye drops, preferably orally. Doses for the prevention or treatment of the abovedescribed complications of diabetes due to an aldose reductase are determined depending upon the desired therapeutic effect, the route of administration, the duration of the treatment, age, body weight and the like. The dose per day for a patient is generally, for example, about 0.1–100 mg/Kg-body weight, preferably about 0.25–5.0 mg/Kg-body weight, for oral administration.

The following Reference Examples and Examples each illustrates one example of the present invention. In the Reference Examples and the Examples, "TLC", "IR", "NMR" and "MS" represent "thin layer chromatography", "infrared absorption spectrum", "nuclear magnetic resonance spectrum" and "mass spectrum", respectively. The ratios of the solvents described in the chromatographic separations are by volume, and the solvents in the parentheses indicate the developing solvents used. Unless specifically described, the infrared absorption spectra are recorded by the liquid film method, and the nuclear magnetic resonance spectra are recorded in deuterochloroform ($CDCl_3$) solution.

Reference Example 1

1 M Aqueous Solution of N-Dithiocarboxyglycine Dipotassium Salt

Carbon disulphide 6 ml was added dropwise to a solution comprising 7.507 g of glycine, 13.2 g of potassium hydroxide and 25 ml of water under ice-cooling while vigorously stirring, followed by stirring at room temperature for 19 hours. The reaction mixture was washed with diethyl ether, and water was added thereto to make the total volume of 100 ml thereby to obtain the titled 1 M solution.

In the same manner, the following 1 M solutions were obtained.

(a) 1 M Aqueous solution of N-dithiocarboxy-α-phenylglycine dipotassium salt (prepared from α-phenylglycine).

(b) 1 M Aqueous solution of N-dithiocarboxy-α,α-dimethylglycine dipotassium salt (prepared from α,α-dimethylglycine).

EXAMPLE 1

3-Carboxymethyl-5-Pentafluorophenylrhodanine

To 1 g of 2-bromo-2-pentafluorophenylacetic acid ethyl ester dissolved in 1.5 ml of ethanol was added 3 ml of the 1 M solution as prepared in Reference Example 1, and the mixture was vigorously stirred at room temperature for 45 minutes. To the mixture was added 1.2 ml of 6 N hydrochloric acid, and the mixture was stirred for 5 minutes. The reaction mixture was extracted with ethyl acetate, and the extract was washed with water, dried over anhydrous magnesium sulphate and concentrated under reduced pressure. The residue was recrystallized from a mixed solvent of cyclohexane, ethyl acetate and hexane to obtain 84 mg of the titled compound.

Melting Point: 215.5°–216.5° C. (recrystallized from cyclohexane-ethyl acetate-hexane).

NMR (acetone-$d_6$+$CDCl_3$ solution): $\delta$=6.1 (1H, s), 4.72 (2H, s).

MS: m/e=357 (M+).

In the same manner, the following compounds were obtained.

(a) 3-Carboxymethyl-5-cyclohexylrhodanine (prepared from 2-bromo-2-cyclohexylacetic acid ethyl ester)

Melting Point: 160°–161° C. (recrystallized from hexane-cyclohexane).

NMR ($CDCl_3$+dimethyl sulfoxide-$d_6$ solution): $\delta$=10.1 (1H, s), 4.72 (2H, s), 4.3 (1H, d), 2.3 (1H, m).

MS: m/e=273 (M+).

(b) 3-Carboxymethyl-5-cyclopentylrhodanine (prepared from 2-bromo-2-cyclopentylacetic acid methyl ester)

Melting Point: 146.5°–147.5° C. (recrystallized from cyclohexane-ethyl acetate-hexane).

NMR ($CDCl_3$+acetone-$d_6$ solution): $\delta$=8.9 (1H, s), 4.72 (2H, s), 4.5 (1H, d), 2.7 (1H, m).

MS: m/e=259 (M+).

(c) 3-(α-Carboxybenzyl)-5-phenylrhodanine (prepared from 2-bromo-2-phenylacetic acid and the 1 M solution of Reference Example 1(a))

Melting Point: 180°–181° C. (recrystallized from ethyl acetate-cyclohexane).

NMR ($CDCl_3$+acetone-$d_6$ solution): $\delta$=7.7–7.2 (10H, m), 6.97 (1H, s), 5.31 (1H, s).

MS: m/e=343 (M+).

(d) 3-(1-Carboxy-1-methyl)ethyl-5-phenylrhodanine (prepared from 2-bromo-2-phenylacetic acid and the 1 M solution of Reference Example 1(b). The purification was performed by silica gel column chromatography using a mixed solvent of cyclohexane and ethyl acetate (4:1) as an eluent)

TLC (cyclohexane:ethyl acetate:acetic acid=10:10:1): Rf=0.58.

IR: $\nu$=1737, 1720, 1496, 1300, 1255, 1152 $cm^{-1}$.

NMR: $\delta$=7.38 (5H, s), 5.14 (1H, s), 2.90 (6H, d).

MS: m/e=295, 279, 209, 168, 123, 118, 91.

(e) 3-Carboxymethyl-5,5-diphenylrhodanine (prepared from 2-bromo-2,2-diphenylacetic acid ethyl ester)

Melting Point: 206°–208° C. (recrystallized from cyclohexane-ethyl acetate-hexane).

NMR ($CDCl_3$+acetone-$d_6$ solution): $\delta$=7.3 (10H, s), 4.8 (2H, s),

MS: m/e=343 (M+).

(f) 3-Carboxymethyl-5-(2-chlorophenyl)rhodanine (prepared from 2-bromo-2-(2-chlorophenyl)acetic acid ethyl ester)

Melting Point: 182°–183° C. (recrystallized from cyclohexane-ethyl acetate-hexane).

NMR (acetone-$d_6$ solution): $\delta$=8.3 (1H, wide s), 7.5 (4H, m), 6.15 (1H, s), 4.85 (2H, s).

MS: m/e=301 (M+).

(g) 3-Carboxymethyl-5-(3-chlorophenyl)rhodanine (prepared from 2-bromo-2-(3-chlorophenyl)acetic acid ethyl ester)

Melting Point: 161°–162° C. (recrystallized from cyclohexane-ethyl acetate).

NMR (acetone-$d_6$ solution): $\delta$=7.7–7.3 (4H, m), 5.85 (1H, s), 4.915 (2H, d).

MS: m/e=301 (M+).

(h) 3-Carboxymethyl-5-(4-chlorophenyl)rhodanine (prepared from 2-bromo-2-(4-chlorophenyl)acetic acid ethyl ester)

Melting Point: 174°–175° C. (recrystallized from cyclohexane-ethyl acetate).

NMR ($CDCl_3$-dimethyl sulfoxide-$d_6$ solution): $\delta$=7.37 (4H, s), 5.4 (1H, s), 4.75 (2H, dd).

MS: m/e=301 (M+).

(i) 3-Carboxymethyl-5-(2,4-dichlorophenyl)rhodanine (prepared from 2-bromo-2-(2,4-dichlorophenyl)acetic acid ethyl ester)

Melting Point: 133°–134° C. (recrystallized from cyclohexane-ethyl acetate-hexane).

NMR: $\delta$=8.2 (1H, s), 7.5–7.3 (3H, m), 5.8 (1H, s), 4.9 (2H, dd).

MS: m/e=335 (M+).

(j) 3-Carboxymethyl-5-(4-nitrophenyl)rhodanine (prepared from 2-bromo-2-(4-nitrophenyl)acetic acid ethyl ester)

Melting Point: 177°–178° C. (recrystallized from cyclohexane-ethyl acetate).

NMR (acetone-$d_6$ solution): $\delta=8.53$ (2H, d), 7.8 (2H, d), 6.1 (1H, s), 4.82 (2H, dd).

MS: m/e=312 (M+).

(k) 3-Carboxymethyl-5-(4-methoxyphenyl)rhodanine (prepared from 2-bromo-2-(4-methoxyphenyl)acetic acid)

Melting Point: 147°–149° C. (recrystallized from cyclohexane-ethyl acetate).

NMR (acetone-$d_6$ solution): $\delta=7.4$ (2H, d), 6.95 (2H, d), 5.75 (1H, s), 4.8 (2H, d), 3.8 (3H, s).

MS: m/e=297 (M+).

(l) 3-Carboxymethyl-5-benzylrhodanine (prepared from 2-bromo-3-phenylpropionic acid ethyl ester)

Melting Point: 186°–186.5° C. (recrystallized from cyclohexane-ethyl acetate-hexane).

NMR (acetone-$d_6$ solution): $\delta=7.32$ (5H, s), 4.95 (1H, dd), 4.7 (2H, s), 3.65 (1H, dd), 3.2 (1H, dd).

MS: m/e=281 (M+).

(m) 3-Carboxymethyl-5-(2-thienyl)rhodanine (prepared from 2-bromo-2-(2-thienyl)acetic acid methyl ester)

TLC (ethyl acetate:cyclohexane:acetic acid=10:10:1): Rf=0.56.

MS: m/e=273 (M+), 227, 155, 128, 124, 96.

EXAMPLE 2

3-Carboxymethyl-5-phenylrhodanine

The 1 M solution (10 ml) as prepared in Reference Example 1 was added to 2.15 g of 2-bromo-2-phenylacetic acid under ice-cooling, and the mixture was stirred at room temperature for 13 hours and concentrated under reduced pressure. To the residue was added 20 ml of toluene, followed by heat-refluxing for 60 minutes. The toluene was removed by decantation. To the residue 10 ml of 1 N hydrochloric acid and 10 ml of water were added, and the mixture was extracted with ethyl acetate. The extract was dried over anhydrous magnesium sulphate and concentrated under reduced pressure. Recrystallization of the residue from cyclohexane and ethyl acetate gave 600 mg of the titled compound.

Melting Point: 158°–159° C. (recrystallized from cyclohexane-ethyl acetate).

NMR (CDCl$_3$+acetone-$d_6$ solution): $\delta=8.45$ (1H, s), 7.35 (5H, s), 5.3 (1H, s), 4.7 (2H, s).

MS: m/e=267 (M+).

In the same manner, the following compounds were obtained.

(a) 3-Carboxymethyl-5,5-dimethylrhodanine (prepared from 2-bromo-2-methylpropionic acid).

Melting Point: 144°–145° C. (recrystallized from cyclohexane).

NMR: $\delta=9.37$ (1H, s), 4.77 (2H, s), 1.7 (6H, s).

MS: m/e=219 (M+).

EXAMPLE 3

3-(3-Carboxypropyl)-5-Phenylrhodanine

To a solution of 2.5 ml of concentrated aqueous ammonia and 0.54 ml of carbon disulfide was added 1.03 g of 4-aminobutanoic acid under ice-cooling, and the mixture was stirred at room temperature for 1 hour and concentrated under reduced pressure. To the residue was added 3 ml of water, and 5 ml of 2 N aqueous solution of sodium 2-bromo-2-phenylacetate was added thereto under ice-cooling, followed by stirring at a temperature of from room temperature to 60° C. for 60 minutes. Concentrated hydrochloric acid (2 ml) was added thereto, and the mixture was stirred at 60° C. for 1 hour and extracted with ethyl acetate. The extract was washed with water, dried over anhydrous sodium sulphate and concentrated under reduced pressure. The residue was purified by silica gel column chromatography using a mixed solvent of cyclohexane and ethyl acetate (3:1) as an eluent to obtain 76 mg of the titled compound.

Melting Point: 138°–139° C. (recrystallized from ethyl acetate-cyclohexane).

NMR (dimethyl sulfoxide-$d_6$ solution): $\delta=7.4$ (5H, s), 5.85 (1H, s), 4.02 (2H, t), 2.29 (2H, t), 1.90 (2H, m).

MS: m/e=295 (M+), 118.

In the same manner, the following compound was obtained.

(a) 3-(1-Carboxyethyl)-5-phenylrhodanine (prepared from 2-aminopropionic acid)

TLC (ethyl acetate): Rf=0.28.

NMR: $\delta=7.35$ (5H, m), 5.7 (1H, m), 5.28 and 5.24 (1H, s in each case), 1.62 and 1.57 (3H, d in each case).

MS: m/e=281 (M+), 84.

EXAMPLE 4

For oral administration, 1000 tablets each containing 50 mg of an active ingredient were prepared from the following compounds according to a known process.

3-Carboxymethyl-5-pentafluorophenylrhodanine—50 g
Sodium citrate—25 g
Alginic acid—10 g
Polyvinyl pyrrolidone—10 g
Magnesium stearate—5 g In the same manner, 1000 tablets each containing 50 mg of an active compound were obtained using the compound of Example 1(g), 1(h), 1(i), 1(j) or 1(k).

We claim:

1. A rhodanine derivative represented by the general formula:

$$\underset{S}{\overset{R^4\quad O}{R^5-\!\!\!\diagup\!\!\!\diagdown\!\!\!\diagup\!\!\!\diagdown}}\;N-(CH_2)_n-\underset{R^3}{\overset{R^2}{C}}-COOR^1 \quad (I)$$

(wherein $R^1$ represents a hydrogen atom or an alkyl group of 1–12 carbon atoms; $R^2$ and $R^3$, which may be the same or different with each other, each represents a hydrogen atom, an alkyl group of 1–4 carbon atoms, or a phenyl group; $R^4$ represents an alkyl group of 1–4 carbon atoms, a cycloalkyl group of 4–7 carbon atoms which is unsubstituted or substituted by at least one alkyl group of 1–4 carbon atoms, a phenyl or benzyl group which is unsubstituted or substituted by halogen atom(s), a trifluoromethyl group, a phenyl group, a nitro group, a hydroxy group, a carboxyl group, an amino group which may be substituted by an alkyl group of 1–4 carbon atoms, or alkyl(s), an alkoxy or an alkylthio group of 1–4 carbon atoms, a naphthyl group, an anthracenyl group, or a 5- or 6-membered heterocyclic ring or a 9- or 10-membered bicyclic fused heterocyclic ring, each containing one nitrogen, oxygen or sulfur atom which is unsubstituted or substituted by halogen atom(s), a trifluoromethyl group, a phenyl group, a nitro group, a hydroxy group, a carboxyl group, an amino group which may be substituted by an alkyl group of 1-4 carbon atoms, or alkyl(s), an alkoxy or an alkylthio group of 1-4 carbon atoms; $R^5$ represents a hydrogen atom, an alkyl gorup of 1-4 carbon atoms, a cycloalkyl group of 4-7 carbon atoms which is unsubstituted or substituted by at least one alkyl group of 1-4 carbon atoms, a phenyl or benzyl group which is unsubstituted or substituted by halogen atom(s), a trifluoromethyl group, a phenyl group, a nitro group, a hydroxy group, a carboxyl group, an amino group which may be substituted by an alkyl group of 1-4 carbon atoms, or alkyl(s), an alkoxy or an alkylthio group of 1-4 carbon atoms, a naphthyl group, an anthracenyl group, or a heterocyclic group containing one of nitrogen, oxygen and sulfur atoms which is unsubstituted or substituted by halogen atom(s), a trifluoromethyl group, a phenyl group, a nitro group, a hydroxy group, a carboxy group, an amino group which may be substituted by an alkyl group of 1-4 carbon atoms, or alkyl(s), an alkoxy or an alkylthio group of 1-4 carbon atoms; n represents 0, 1 or 2; with the proviso that when $R^5$ represents a hydrogen atom or an alkyl group of 1-4 carbon atoms, $R^4$ does not represent an alkyl group of 1-4 carbon atoms) or when $R^1$ represents a hydrogen atom, a non-toxic salt of the acid.

2. A compound as described in claim 1, which is 3-carboxymethyl-5-pentafluorophenylrhodanine.

3. A compound as described in claim 1, which is 3-carboxymethyl-5-cyclohexylrhodanine.

4. A compound as described in claim 1, which is 3-carboxymethyl-5-cyclopentylrhodanine.

5. A compound as described in claim 1, which is 3-(α-carboxybenzyl)-5-phenylrhodanine.

6. A compound as described in claim 1, which is 3-(1-carboxy-1-methyl)ethyl-5-phenylrhodanine.

7. A compound as described in claim 1, which is 3-carboxymethyl-5,5-diphenylrhodanine.

8. A compound as described in claim 1, which is 3-carboxymethyl-5-(2-chlorophenyl)rhodanine.

9. A compound as described in claim 1, which is 3-carboxymethyl-5-(3-chlorophenyl)rhodanine.

10. A compound as described in claim 1, which is 3-carboxymethyl-5-(4-chlorophenyl)rhodanine.

11. A compound as described in claim 1, which is 3-carboxymethyl-5-(2,4-dichlorophenyl)rhodanine.

12. A compound as described in claim 1, which is 3-carboxymethyl-5-(4-nitrophenyl)rhodanine.

13. A compound as described in claim 1, which is 3-carboxymethyl-5-(4-methoxyphenyl)rhodanine.

14. A compound as described in claim 1, which is 3-carboxymethyl-5-benzylrhodanine.

15. A compound as described in claim 1, which is 3-carboxymethyl-5-phenylrhodanine.

16. A compound as described in claim 1, which is 3-(3-carboxypropyl)-5-phenylrhodanine.

17. A compound as described in claim 1, which is 3-(1-carboxyethyl)-5-phenylrhodanine.

18. A compound as described in claim 1, which is 3-carboxymethyl-5-(2-thienyl)rhodanine.

19. An aldose reductase inhibitor comprising, as a main ingredient, an effective amount of at least one of rhodanine derivatives represented by the general formula:

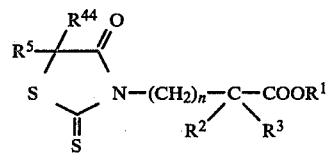

(wherein $R^1$ represents a hydrogen atom or an alkyl group of 1-12 carbon atoms; $R^2$ and $R^3$, which may be the same or different with each other, each represents a hydrogen atom, an alkyl group of 1-4 carbon atoms, or a phenyl group; $R^{44}$ represents an alkyl group of 1-4 carbon atoms, a cycloalkyl group of 4-7 carbon atoms which is unsubstituted or substituted by at least one alkyl group of 1-4 carbon atoms, a phenyl or benzyl group which is unsubstituted or substituted by halogen atom(s), a trifluoromethyl group, a phenyl group, a nitro group, a hydroxy group, a carboxyl group, an amino group which may be substituted by an alkyl group of 1-4 carbon atoms, or alkyl(s), an alkoxy or an alkylthio group of 1-4 carbon atoms, a naphthyl group, an anthracenyl group, or a 5- or 6-membered heterocyclic ring or a 9- or 10-membered bicyclic fused heterocyclic ring, each containing one nitrogen, oxygen or sulfur atom which is unsubstituted or substituted by halogen atom(s), a trifluoromethyl group, a phenyl group, a nitro group, a hydroxy group, a carboxyl group, an amino group which may be substituted by an alkyl group of 1-4 carbon atoms, or alkyl(s), an alkoxy or an alkylthio group of 1-4 carbon atoms; $R^5$ represents a hydrogen atom, an alkyl group of 1-4 carbon atoms, a cycloalkyl group of 4-7 carbon atoms which is unsubstituted or substituted by at least one alkyl group of 1-4 carbon atoms, a phenyl or benzyl group which is unsubstituted or substituted by halogen atom(s), a trifluoromethyl group, a phenyl group, a nitro group, a hydroxy group, a carboxyl group, an amino group which may be substituted by an alkyl group of 1-4 carbon atoms, or alkyl(s), an alkoxy or an alkylthio group of 1-4 carbon atoms, a naphthyl group, an anthracenyl group, or a heterocyclic group containing one of nitrogen, oxygen and sulfur atom which is unsubstituted or substituted by halogen atom(s), a trifluoromethyl group, a phenyl group, a nitro group, a hydroxy group, a carboxy group, an amino group which may be substituted by an alkyl group of 1-4 carbon atoms, or alkyl(s), an alkoxy or an alkylthio group of 1-4 carbon atoms; n represents 0, 1 or 2; with the proviso that when $R^5$ represents a hydrogen atom, $R^{44}$ does not represent an alkyl group of 1-4 carbon atoms) with pharmaceutically acceptable carrier.

20. An aldose reductase inhibitor as described in claim 19, which is for preventing or treating nerve disturbances caused by an aldose reductase.

21. An aldose reductase inhibitor as described in claim 19, which is for preventing or treating retinopathy caused by an aldose reductase.

22. An aldose reductase inhibitor as described in claim 19, which is for preventing or treating diabetic cataract caused by an aldose reductase.

23. An aldose reductase inhibitor as described in claim 19, which is for preventing or treating renal disturbances caused by an aldose reductase.

24. An aldose reductase inhibitor as described in any of claims 19, 20, 21, 22, or 23, which is pharmaceutical composition for oral administration.

25. An aldose reductase inhibitor as described in any of claims 19, 20, 21, 22, 23, or 24, which is orally administered at a dose of about 0.1–100 mg/Kg-body weight per day.

26. A rhodanine derivative as described in claim 1, wherein $R^4$ represents an alkyl group of 1-4 carbon atoms.

27. A rhodanine derivative as described in claim 1, wherein $R^4$ represents a cycloalkyl group of 4-7 carbon atoms which is unsubstituted or substituted by at least one alkyl group of 1-4 carbon atoms.

28. A rhodanine derivative as described in claim 1, wherein $R^4$ represents a phenyl or benzyl group which is unsubstituted or substituted by at least one halogen atom or alkyl group of 1-4 carbon atoms.

29. A rhodanine derivative as described in claim 1, wherein $R^4$ represents a phenyl or benzyl group which is substituted by a trifluoromethyl group, a phenyl group, a nitro group, a hydroxy group, a carboxyl group, an amino group which may be substituted by an alkyl group of 1-4 carbon atoms, or an alkoxy or an alkylthio group of 1-4 carbon atoms.

30. A rhodanine derivative as described in claim 1, wherein $R^4$ represents a naphthyl group or an anthracenyl group.

31. A rhodanine derivative as described in claim 1, wherein $R^4$ represents a heterocyclic group containing one of nitrogen, oxygen and sulfur atom which unsubstituted or substituted by at least one halogen atom or alkyl group of 1-4 carbon atoms.

32. A rhodanine derivative as described in any one of claims 27 to 31, wherein $R^5$ represents a hydrogen atom, an alkyl group of 1-4 carbon atoms, or a phenyl group.

33. A method of preventing or treating nerve disturbances, retinopathy, diabetic cataract or renal disturbances caused by an aldose reductase in mammals which comprises administering a therapeutically effective amount of at least one rhodanine derivative represented by the general formula:

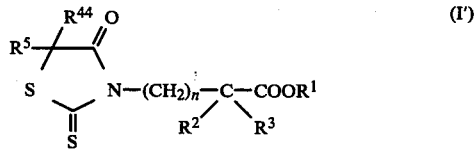

(I')

(wherein $R^1$ represents a hydrogen atom or an alkyl group of 1-12 carbon atoms; $R^2$ and $R^3$, which may be the same or different with each other, each represents a hydrogen atom, an alkyl group of 1-4 carbon atoms, or a phenyl group; $R^{44}$ represents an alkyl group of 1-4 carbon atoms, a cycloalkyl group of 4-7 carbon atoms which is unsubstituted or substituted by at least one alkyl group of 1-4 carbon atoms, a phenyl or benzyl group which is unsubstituted or substituted by halogen atom(s), a trifluoromethyl group, a phenyl group, a nitro group, a hydroxy group, a carboxyl group, an amino group which may be substituted by an alkyl group of 1-4 carbon atoms, or alkyl(s), an alkoxy or an alkylthio group of 1-4 carbon atoms, a naphthyl group, an anthracenyl group, or a 5- or 6-membered heterocyclic ring or a 9- or 10-membered bicyclic fused heterocyclic ring, each containing one nitrogen, oxygen or sulfur atom which is unsubstituted or substituted by halogen atom(s), a trifluoromethyl group, a phenyl group, a nitro group, a hydroxy group, a carboxyl group, an amino group which may be substituted by an alkyl group of 1-4 carbon atoms, or alkyl(s), an alkoxy or an alkylthio group of 1-4 carbon atoms; $R^5$ represents a hydrogen atom, an alkyl group of 1-4 carbon atoms, a cycloalkyl group of 4-7 carbon atoms which is unsubstituted or substituted by at least one alkyl group of 1-4 carbon atoms, a phenyl or benzyl group which is unsubstituted or substituted by halogen atom(s), a trifluoromethyl group, a phenyl group, a nitro group, a hydroxy group, a carboxyl group, an amino group which may be substituted by an alkyl group of 1-4 carbon atoms, or alkyl(s), an alkoxy or an alkylthio group of 1-4 carbon atoms, a naphthyl group, an anthracenyl group, or a heterocyclic group containing one of nitrogen, oxygen and sulfur atom which is unsubstituted or substituted by halogen atom(s), a trifluoromethyl group, a phenyl group, a nitro group, a hydroxy group, a carboxy group, an amino group which may be substituted by an alkyl group of 1-4 carbon atoms, or alkyl(s), an alkoxy or an alkylthio group of 1-4 carbon atoms; n represents 0, 1 or 2; with the proviso that when $R^5$ represents a hydrogen atom, $R^{44}$ does not represent an alkyl group of 1-4 carbon atoms) or when $R^1$ represents a hydrogen atom, a non-toxic salt of the acid.

34. A method as described in claim 33, which comprises administering a therapeutically effective amount of at least one rhodanine derivative as described in claim 33, wherein $R^{44}$ represents an alkyl group of 1-4 carbon atoms.

35. A method as described in claim 33, which comprises administering a therapeutically effective amount of at least one rhodanine derivative as described in claim 33, wherein $R^{44}$ represents an cycloalkyl group of 4-7 carbon atoms which is unsubstituted or substituted by at least one alkyl group of 1-4 carbon atoms.

36. A method as described in claim 33, which comprises administering a therapeutically effective amount of at least one rhodanine derivative as described in claim 33, wherein $R^{44}$ represents a phenyl or benzyl group which is unsubstituted or substituted by at least one halogen atom or alkyl group of 1-4 carbon atoms.

37. A method as described in claim 33, which comprises administering a therapeutically effective amount of at least one rhodanine derivative as described in claim 33, wherein $R^{44}$ represents a phenyl or benzyl group which is substituted by a trifluoromethyl group, a phenyl group, a nitro group, a hydroxy group, a carboxyl group, an amino group which may be substituted by an alkyl group of 1-4 carbon atoms, or an alkoxy or alkylthio group of 1-4 carbon atoms.

38. A method as described in claim 33, which comprises administering a therapeutically effective amount of at least one rhodanine derivative as described in claim 33, wherein $R^{44}$ represents a naphthyl group or an anthracenyl group.

39. A method as described in claim 33, which comprises administering a therapeutically effective amount of at least one rhodanine derivative as described in claim 33, wherein $R^{44}$ represents a heterocyclic group containing one of nitrogen, oxygen and sulfur atoms which is unsubstituted or substituted by at least one halogen atom or alkyl group of 1-4 carbon atoms.

40. A method as described in claim 33, which comprises administering a therapeutically effective amount of at least one rhodanine derivative as described in claim 34, wherein $R^5$ represents an alkyl group of 1-4 carbon atoms or a phenyl group.

41. A method as described in claim 33, which comprises administering a therapeutically effective amount of at least one rhodanine derivative as described in any one of claims 35 to 39, wherein $R^5$ represe represents a hydrogen atom, an alkyl group of 1-4 carbon atoms or a phenyl group.

* * * * *